United States Patent [19]

Sorensen et al.

[11] Patent Number: 4,892,405

[45] Date of Patent: Jan. 9, 1990

[54] METHOD AND APPARATUS FOR PROVIDING QUALITY ASSURANCE AND CALIBRATION ASSURANCE IN A SPECTROPHOTOMETER

[75] Inventors: Keld Sorensen; James N. Macri; Timothy J. Douros, all of Oyster Bay; Paul Sajda, Commack; Emiddio V. Ippolito, Smithtown, all of N.Y.

[73] Assignee: NTD Laboratories, Inc., Carle Place, N.Y.

[21] Appl. No.: 256,568

[22] Filed: Oct. 12, 1988

[51] Int. Cl.$^4$ .................. G12B 13/00; G01N 21/59
[52] U.S. Cl. ................................. 356/243; 356/434
[58] Field of Search ............... 356/243, 408, 409, 434, 356/435, 436

[56] References Cited

U.S. PATENT DOCUMENTS 3,762,817 10/1973 Harklau .................... 356/434 X
3,773,426 11/1973 Mudd ........................ 356/434
4,059,357 11/1977 Klein ......................... 356/243

Primary Examiner—Davis L. Willis
Assistant Examiner—Matthew W. Koren
Attorney, Agent, or Firm—Kenyon & Kenyon

[57] ABSTRACT

An apparatus for the calibration and quality assurance of a multichannel spectrophotometer, particularly an ELISA spectrophotometer, comprises a series of filters having a known first color and linearly increasing optical density. The response of the spectrophotometer is measured against the known color and linearly increasing optical density. Additional filters of at least one additional color permit checking the color response of the spectrophotmeter. An algorithm determines whether the response conforms to predetermined conditions. An output is produced to provide a record of the calibration and quality assurance of the spectrophotometer. The invention has particular utility for conducting calibration and quality assurance of ELISA spectrophotometers used in clinical laboratory screening for infectious diseases, such as Hepatitis B and the AIDS viruses.

11 Claims, 5 Drawing Sheets

FIG. 2

COLUMN → 1 2 3 4 5 6 7 8 9 10 11 12

ROW ↓

FIG. 3

1 2 3 4 5 6 7 8 9 10 11 12
COLUMN →

METHOD AND APPARATUS FOR PROVIDING QUALITY ASSURANCE AND CALIBRATION ASSURANCE IN A SPECTROPHOTOMETER

BACKGROUND OF THE INVENTION

The present invention relates to a method and apparatus for the calibration and quality control of a spectrophotometer and particularly an ELISA spectrophotometer used in a clinical laboratory.

Spectrophotometers are a well known tool in the analytical chemistry laboratory. One type of commercially available spectrophotometer is the ELISA spectrophotometer which typically comprises a plurality of light sources and detectors commonly arranged in a column of eight. The ELISA typically operates at one of two discrete wavelengths, such as 405 nm and 492 nm corresponding to yellow and red, respectively. The ELISA spectrophotometer can be used to analyze the photometric density produced by assay of biological materials. These assays are arranged as an assay plate having a number of rows corresponding to the number of channels of the ELISA spectrophotometer and a number of columns. Typically the ELISA spectrophotometer comprises an 8×12 matrix of 96 cells. The ELISA spectrophotometer now typically includes a microprocessor analyzing and recording the output of each channel for each assay well of a sample plate.

The ELISA spectrophotometer is a relatively recent addition to the analytical laboratory. An even more recent development has been the introduction of the ELISA spectrophotometer into the clinical laboratory. The immuno-chemical identification of exposure to hepatitis B virus, the Herpes virus, and the HIV virus, the "AIDS" virus, uses an ELISA spectrophotometer. The significance of photometric measurements made with an ELISA spectrophotometer now have implications that directly relate to the control of infectious epidemics. The measurement integrity of an ELISA spectrophotometer is therefore a matter of considerable concern to laboratory technicians, regulatory agencies and the general public.

The ELISA spectrophotometers used in clinical laboratories, however, are not equipped to insure proper calibration or quality control. Calibration is defined as the integrity of the normal operation of the instrument and relates to the spectrophotometer itself. Quality assurance is defined as the integrity of the results produced by a laboratory technician using a properly functioning spectrophotometer. At present, the calibration of an ELISA spectrophotometer is established once at the factory when manufactured. No provision is made for confirming calibration after the spectrophotometer leaves the factory. Quality assurance is left to each individual clinical laboratory and laboratory technician.

The calibration of an ELISA spectrophotometer can be compromised through both electronic and optical errors. Electrical errors arise from a variety of causes. An ELISA spectrophotometer employs filters of predetermined density and color. An electronic mechanism selects among the filters. A failure in the selection mechanism may result in the wrong filter being inserted. A laboratory technician would not notice the malfunction even if he could view the filter.

Alternately, the electronic memory that serves the microprocessor of the ELISA spectrophotometer may fail. Such a failure would most likely remain undetected using current calibration techniques. At present, an ELISA is calibrated by "blanking" the channels to establish a base line for zero optical density. A defective memory would likely read zero during "blanking". Nothing about the reading would necessarily indicate that the ELISA was defective. A memory defect used in the context of HIV screening would preclude the production of any positive test results. Individuals exposed to a virus would test free of infection whether or not such is true.

Yet another source of electronic error is the connection between the ELISA spectrophotometer and its microprocessor. The microprocessor of a personal computer often analyzes the output of the ELISA spectrophotometer and serves as the microprocessor for the ELISA. The transmission line between the spectrophotometer and personal computer normally uses a "handshake" protocol in which the photometer generates a check sum which is then exchanged with the computer. However, most programs used to analyze the output of an ELISA spectrophotometer do not analyze the check sum. Any transmission error thus goes unrecognized.

Optical errors can originate from a number of sources. For example, dust can obstruct a channel of an ELISA spectrophotometer and thus reduce its throughput efficiency. Alternately, the light source for a particular channel may become erratic and produce "jumps" in output or "burn hot" and produce a consistently high signal. This type of erratic output cannot be corrected using baseline subtraction.

Yet another source of potential optical error involves the deterioration of the filters of the ELISA spectrophotometer. This deterioration can take many forms such as, for example, the formation of cracks. Filter deterioration which is not necessarily noticed by the human eye can nevertheless give erroneous readings.

Optical errors can produce either false positives or false negatives depending on the test being run. The resulting misdiagnosis is traumatic to the patient involved and results in a substantial expenditure of time and resources to correct.

A second type of error in an ELISA spectrophotometer measurement is human error. A filter could be improperly inserted due to any number of reasons such as improper labeling or a defective selecting mechanism. A laboratory technician also could select the wrong filter for a given measurement. In either event, the error is not readily apparent using base line substraction because the values of the baseline measurements are substantially lower than those corresponding to a sample. Inserting the wrong filter causes all samples in a particular assay to appear "normal". The purpose of the assay is compromised and individuals are again diagnosed as being free of infectious diseases whether or not such is true.

The near total absence of calibration and quality assurance controls for ELISA spectrophotometers is uncharacteristic of the clinical laboratory. Stringent governmental regulation is more the norm than the exception. These regulations typically include frequently documented calibration tests of pipettes, scales, etc. Records must also be kept documenting preventative maintenance performed on the equipment as well as record that identify the equipment used to obtain the quality control and calibration measurements. For example, radiochemical procedures use a stable radioisotopes in combination with the counting equipment for daily quality assurance and calibration measurements.

Records are maintained for review by the appropriate government regulatory agency. Likewise, test tube immunochemical procedures employ a series of sealed test tubes having dilutions of known color for use in a one channel photometer. The quality assurance measurements and calibrations are comparable to that required for radiochemical procedures.

The quality assurance and calibration confirmation procedures employed with a single channel photometer are not adequate for more complicated clinical procedures. For example, primitive "spot-check" calibration and baseline measurements are adequate for an ELISA spectrophotometer when used in an analytical laboratory. A skilled researcher could readily determine if his equipment or his procedure were defective since he would be highly familiar with the equipment and would have some idea of what result to expect. However, the clinical laboratory technician must analyze unknown samples without intuition. Errors are not apparent. Any errors on spectrophotometric measurement become matters of public health concern rather than strictly setbacks to research.

A need exists in the art for a method and apparatus for the calibration and quality assurance of ELISA and similar spectrophotometers that will work reliably and quickly in a clinical laboratory.

SUMMARY OF THE INVENTION

The present invention relates to an apparatus for the calibration and quality assurance of a multichannel spectrophotometer, particularly an ELISA spectrophotometer. The apparatus is particularly well adapted for use in a clinical laboratory which performs many repetitive tests on unknown samples. The invention allows the clinical laboratory to keep detailed records of the type normally required by governmental regulatory authorities.

The invention uses a series of filters that have a known first color and linearly increasing optical density. The calibration of the photometer is measured against the known increase in optical density. An additional one or more filters of a second color permits checking the color response of the spectrophotometer. An algorithm determines whether the response follows a linear increase in the optical density of the first color and records an appropriate increase in optical density using filters of the second color.

The present invention has particular applicability to ELISA spectrophotometry. A QC plate is formed by inserting the filters of the first and second color into the wells of an ELISA sample holder. The ELISA sample holder typically comprises a 8×12 matrix of 96 individual sample wells. The 12 columns of the sample plate permit adding multiple filters for each optical density and color as well as two columns of zero optical density for each row of the photometer. The color filters are obtained from readily available commercial plastic. Test results of high quality are easily obtained at minimal cost. The optical density of the first color is linearly increased by adding additional layers of filter material to a given sample well. The QC plate is thus highly accurate while also being extremely low in cost to produce as well as simple and rugged.

The signals generated by the detectors of the ELISA spectrophotometer using the QC plate are analyzed using algorithms written in the form of a software program and executed on an appropriate computer such as a microprocessor. These algorithms are designed to assure the integrity and consistency. The resulting output is a combined calibration and quality control analysis that instantly informs an operating technician whether the ELISA spectrophotometer is free of a large number of potential sources of error. The resulting output can be printed and retained to satisfy typical governmental regulatory requirements.

BRIEF DESCRIPTION OF THE DRAWINGS

FIG. 2 shows a QC plate for an ELISA spectrophotometer;

FIG. 3 shows a cross section of the sample plate shown in FIG. 2; and

DETAILED DESCRIPTION

Figure 1:
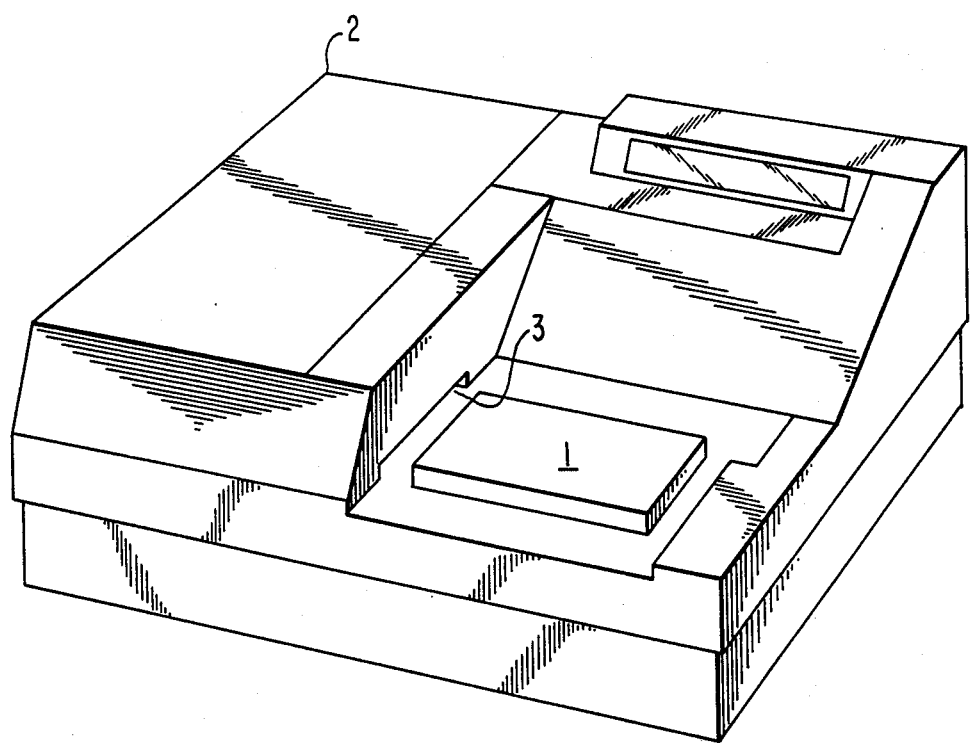
FIG. 1 shows an ELISA spectrophotometer.

FIG. 1 shows a conventional ELISA spectrophotometer, EAR 400 FW, manufactured by SLT Labinstruments G.m.b.H, of A-5082 Grodig/Salzburg, Austria. The sample holder 1 is shown in a position prior to being read by the ELISA spectrophotometer after being fed into the spectrophotometer through a slot 3.

FIG. 2 shows an enlarged view from the top of sample plate 1 of the type shown in FIG. 1. Sample plate 1 comprises a plurality of sample wells arranged in a matrix of 8 rows and 12 columns as shown. The configuration of an 8×12 matrix is standard for an ELISA spectrophotometer. The sample wells shown in FIG. 1 hold a plurality of filters. Columns 1 and 2 contain a zero optical density filter that can be produced most simply by leaving each sample well empty. Columns 3–10 contain linearly increasing densities of the first color optical filter. Columns 11 and 12 contain filters of the second color.

FIG. 3 shows a cross section of the sample plate shown in FIG. 1. Columns 3 and 4 are shown to contain a first thickness of the first color. Likewise, columns 5 and 6 contain two layers of the first color filter. The absorbence of columns 5 and 6 will therefore be twice the absorbence of columns 3 and 4. Columns 7 and 8 likewise contain 3 layers of the first color optical filter. The optical density of columns 7 and 8 is therefore three times greater than columns 2 and 3 and half again greater than the density columns 4 and 5. Columns 9 and 10 likewise contain four layers of the first color optical material and have an optical density four times greater than columns 3 and 4, twice as great as columns 5 and 6, and a third greater than columns 7 and 8. A linear increase in the optical density of the first color optical filters is thus obtained by linearly increasing the thickness of the filters of the first color. Columns 11 and 12 contain a single layer of a second color filter.

Figure 4:
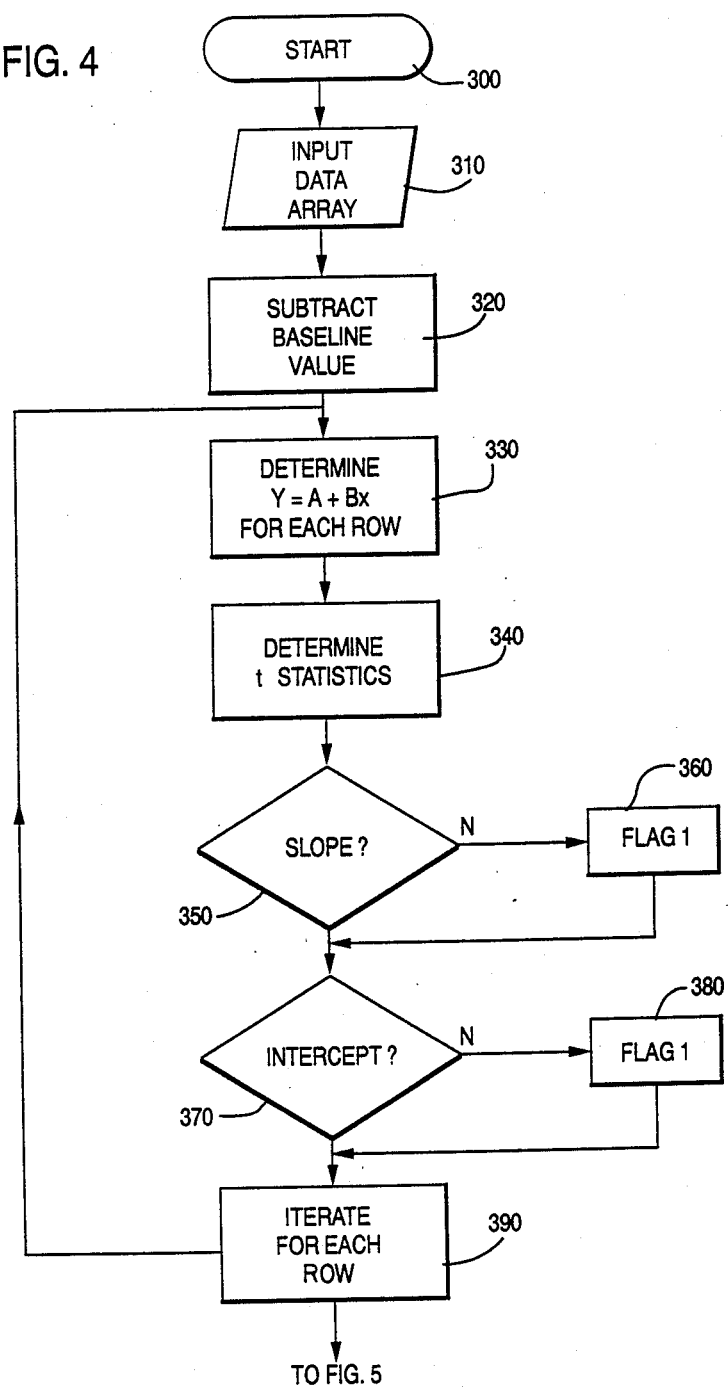
FIGS. 4–6 show a flow chart for analyzing the output of the spectrophotometer generated using the sample plate shown in FIGS. 2 and 3.
Figure 5:
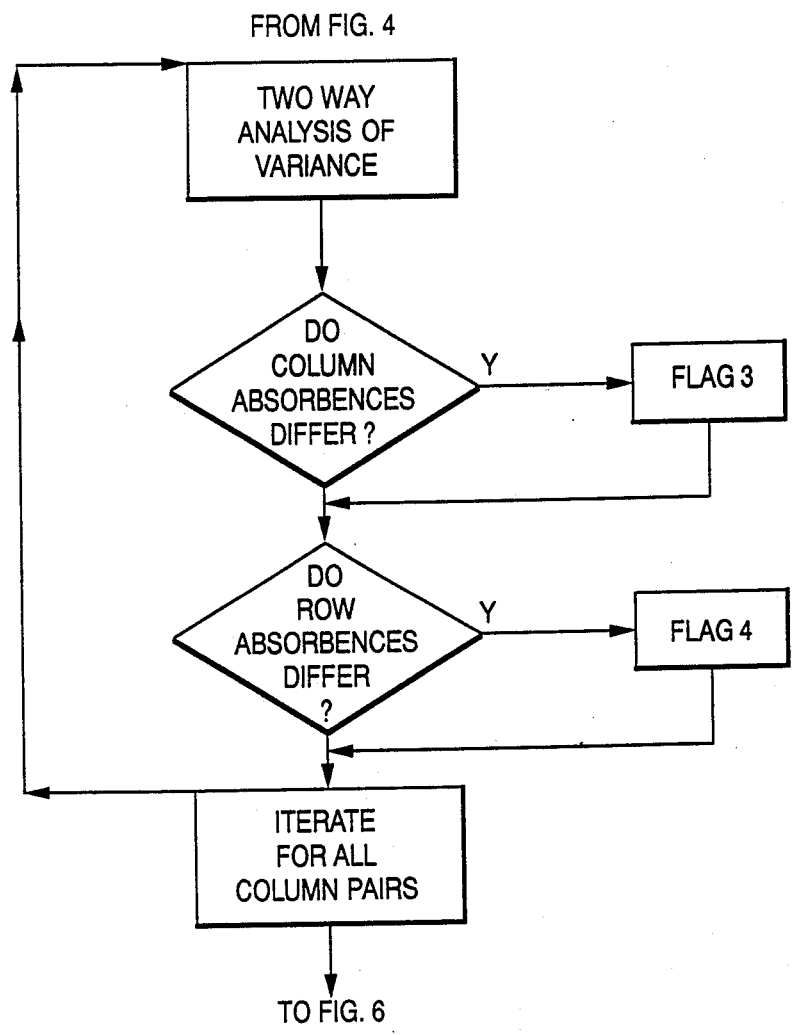
Figure 6:
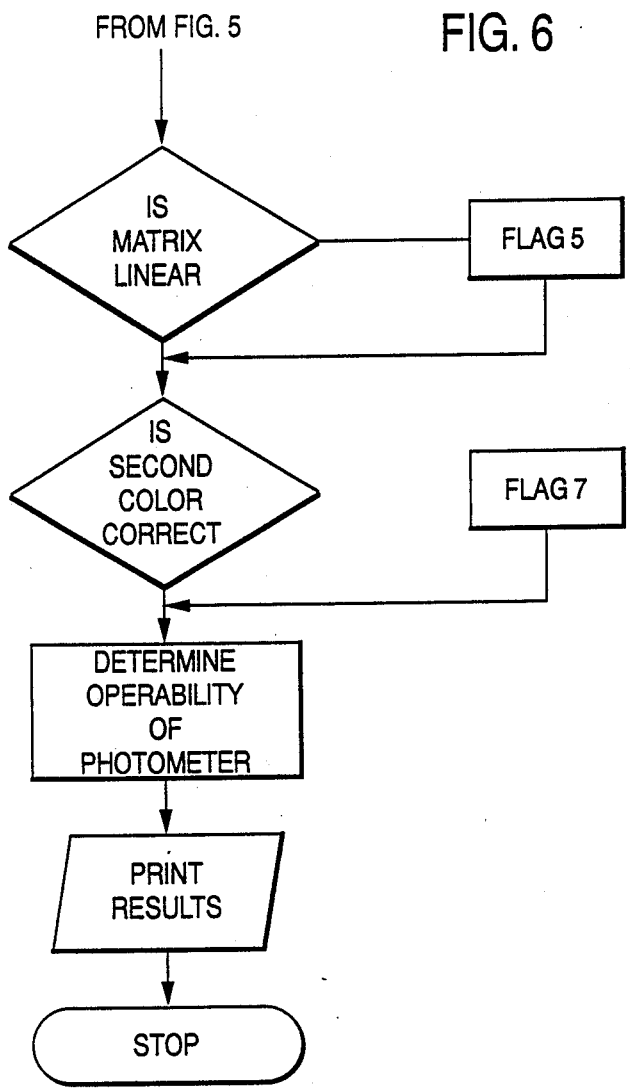

FIGS. 4–6 show the flow chart for the preferred analysis to be conducted on the output of the ELISA spectrophotometer using the QC plate shown in FIGS. 2 and 3. The flowcharts implement mathematical operations that are well known in the art as found in Walpole, et al., *Probability and Statistics for Engineer and Scientists*, McMillan, Inc. (1985), incorporated herein by reference.

Referring to FIG. 4, the program starts at step 300 and inputs an array of numbers at step 310. The array corresponds to the absorbence values obtained from each sample well of the QC plate. The data is stored in a 96 element matrix for the standard 8×12 well sample plate shown in FIG. 2. The absorbence values from the 16 elements in the first two columns is averaged and subtracted from each element in the matrix at step 320. This step constitutes the conventional baseline measurement used in prior art analysis routines.

The program of the present invention proceeds to determine a linear regression at step 330 for each row of the matrix, corresponding to at least one channel of the spectrophotometer. The values for the linearly increasing optical density filters are compared against a linear model in the form $Y=A+Bx$. A statistical determination of the slope for columns 1-10 of each row is computed at step 340. The comparison is performed for each row of the array having linearly increasing optical density filters. The necessary t statistics are determined at step 340. These mathematical operations are known in the art and disclosed, for example, on pages 315-31 of Walpole, et al. Whether the slope corresponds to the known value is determined at step 350. If not, flag 1 is set at step 360. At step 370, the Y intercept is compared against its predetermined value of zero. At step 390 the process is reiterated for each row of the QC plate.

Referring to FIG. 5, a two way analysis of variance is conducted on the measurements from the zero optical density filters at step 500. The analysis of variance determination is known in the art ad disclosed, for example, on pages 393-444 of Walpole, et al. The data for the zero density optical filters in the first column are analyzed to determine whether the average of the first column is significantly different than the average absorbence of the second column. If it is, then a defect exists and flag 3 is set at step 520. Step 530 represents the determination of whether the average absorbence of any row in the first column pair is significantly different than the average absorbence of any other row in the first column pair. The significance test itself is known in the art as disclosed, for example, on pages 274-279 of Walpole, et al. If the average values are significantly different, the spectrophotometer is not operating correctly and flag 4 is set at step 540. Step 550 indicates that the process is iterated for each column pair of the test data from the QC plate.

Referring to FIG. 6, a conditional step 600 determines whether the absorbence values from the linearly increasing optical density filters really do increase linearly using an analysis of variance on a linear regression model for rows 1-8 and columns 1-10. If not, the spectrophotometer is not operating properly and a flag 5 is set at step 610. A non-linear operation of the photometer indicates that it is not operating properly because the QC plate should generate a linear response. Finally, whether the average absorbence values obtained using the second color optical density filter is significantly different from a predetermined standard absorbence value is determined at step 640. If there is a significant difference, the spectrophotometer is not operating properly and flag 7 is set at step 650. This analysis is performed for each row of the spectrophotometer. Flags 1-7 are analyzed at step 660. An output is generated at step 670 to indicate whether the photometer is operational. If any of flags 1-7 are set, the output will indicate that the photometer is not operational. Further, the flags 1-7 can be used to generate diagnostic codes to help in determining the source of error in the spectrophotometer.

The foregoing program can be implemented on a standard personal computer. The PC receives its input directly from the spectrophotometer and generates its output using a standard printer. The use of a PC to control an ELISA spectrophotometer is well known in the art.

The foregoing QC plate has numerous advantages over the prior art. Specifically, the sample wells of the QC plate correspond in number and location to those used to make laboratory observations. The ability of the spectrophotometer to position the QC plate is thus checked along with the additional electrical and optical error sources noted in the background to this invention. The accuracy of the calibration and quality assurance check obtained with the ELISA spectrophotometer thus have the accuracy and stability over time normally expected of a clinical laboratory.

The principles, preferred embodiments and modes of operation of the present invention have been described in the foregoing specification. The invention which is intended to be protected herein should not, however, be construed as limited to the particular forms described as these are to be regarded as illustrative rather than restrictive. Variations and changes may be made by those skilled in the art without departing from the spirit of the invention. Accordingly, the foregoing detailed description should be considered exemplary in nature and not as limiting to the scope and spirit of the invention set forth in the appended claims.

What is claimed is:

1. A quality monitoring apparatus for a photometer used to sample a plurality of samples, the photometer having at least one light source and at least one detector for generating signals corresponding to light from the samples, comprising:
   a QC plate having an array of sample wells, at least some of said sample wells having different optical densities of a known value and first color between the source and detector, the array serving to position a sample well of the QC plate at each location at which the photometer samples one of the plurality of samples;
   means for processing the signals generated when each density of the first color is sampled; and
   means for indicating from the processed signals whether the photometer is operational.

2. A quality monitoring apparatus as claimed in claim 1, wherein:
   the sample wells of the QC plate comprise a plurality of filters having different optical densities of the first color; and
   the processing means comprises means for processing the signal according to a predetermined algorithm.

3. A quality monitoring apparatus as claimed in claim 2, wherein the sample wells of the QC plate comprise filters having a second color between the light source and the detector.

4. A quality monitoring apparatus as claimed in claim 3, wherein the photometer comprises a plurality of channels, each channel having a plurality of sources and detectors.

5. A quality monitoring apparatus as claimed in claim 4, wherein the filters of said first and second colors are arranged on the QC plate in apertures in which the filters are mounted, the filters of the second color forming at least one column, the filters of the same optical density forming at least one column each, the filters of the first and second colors forming a matrix on the plate.

6. A quality monitoring apparatus as claimed in claim 5, wherein the photometer is an ELISA spectrophotometer.

7. A quality monitoring apparatus as claimed in claim 6, wherein the QC plate further comprises an additional column of zero optical density filters.

8. A quality monitoring apparatus as claimed in claim 7, wherein the QC plate comprises an eight by twelve matrix comprising two columns each of zero optical density filters, the second color filters and each optical density of the first color filters.

9. A quality monitoring apparatus as claimed in claim 8, wherein the optical density of the filters of the first color increase linearly sequentially.

10. A quality monitoring apparatus as claimed in claim 9, wherein the linear increase in the optical density of the filters is obtained by linearly increasing the thickness of material having a known optical density at the first color.

11. A quality monitoring apparatus as claimed in claim 8, wherein the algorithm executes subroutines chosen from the group consisting of:

a linear regression analysis of at least one channel of the photometer to determine whether the signals of each channel indicate that the photometer is measuring a predetermined rate of change in the optical density of the filters in a way that is also free of systematic error;

a first color variance analysis to determine whether the at least one channel of the photometer is measuring the same optical density for filters of the first color that have the same optical density;

a second color variance analysis to determine whether the at least one channel of the photometer is measuring the same optical density for filters of the second color that have the same optical density;

an analysis of variance of a linear regression model to determine whether the photometer is responding linearly to the linearly increasing optical density filters of first colors;

a significance test to determine whether the values obtained using the second color filters are significantly different from a predetermined standard value; and a significance test to determine whether all detectors of the photometer are measuring an average value of substantially zero with the zero optical density filters.

* * * * *